United States Patent [19]

Perrett et al.

[11] 4,267,939
[45] May 19, 1981

[54] MEDICAL DEVICE STERILIZATION CASE

[75] Inventors: Thomas R. Perrett, Bala Cynwyd, Pa.; Gilbert T. Carter, Oaklandon, Ind.

[73] Assignee: Synthes AG, Chur, Switzerland

[21] Appl. No.: 65,530

[22] Filed: Aug. 10, 1979

[51] Int. Cl.³ .............................................. B65D 45/00
[52] U.S. Cl. .................................. 220/318; 220/331; 220/367; 220/94 R
[58] Field of Search .............. 220/297, 300, 303, 318, 220/331, 346, 367, 94 R

[56] References Cited

U.S. PATENT DOCUMENTS

| | | | |
|---|---|---|---|
| 2,804,986 | 9/1957 | Jeffers et al. | 220/331 |
| 3,080,996 | 3/1963 | Graham | 220/318 |
| 3,471,054 | 10/1969 | Ostrowsky et al. | 220/318 |
| 3,741,433 | 6/1973 | Bentley et al. | 220/318 |
| 4,158,421 | 6/1979 | Chi | 220/331 |

Primary Examiner—Joseph Man-Fu Moy
Attorney, Agent, or Firm—Davis, Hoxie, Faithfull & Hapgood

[57] ABSTRACT

A sterilization case comprises a top wall member having a pair of depending side walls, a bottom wall member having a pair of upstanding front and rear walls, upstanding post members disposed at each side edge of the front and rear walls and attached to the front and rear walls and a handle member pivotally attached to each side wall with its axis of rotation and its longitudinal axis parallel to the longitudinal axis of its associated side wall and with a portion of it pivotally disposable between adjacent associated posts affixed to the front and rear walls. Each post comprises a neck extending above the upper edge of the front and rear walls and a head surmounting the neck whose minimum transverse dimension is greater than the maximum transverse dimension of the neck, and the top wall has a pair of recesses extending rearwardly from its front edge and a pair of apertures disposed adjacent its rear edge. Each recess and aperture is provided with a concave extension at its rear edge configured to underly the head and restrain upward movement of the top wall. The longitudinal dimension of the handle is approximately equal to the distance between associated posts affixed to the front and walls so that the handle can prevent rearward sliding movement of the top wall and its associated side walls.

3 Claims, 6 Drawing Figures

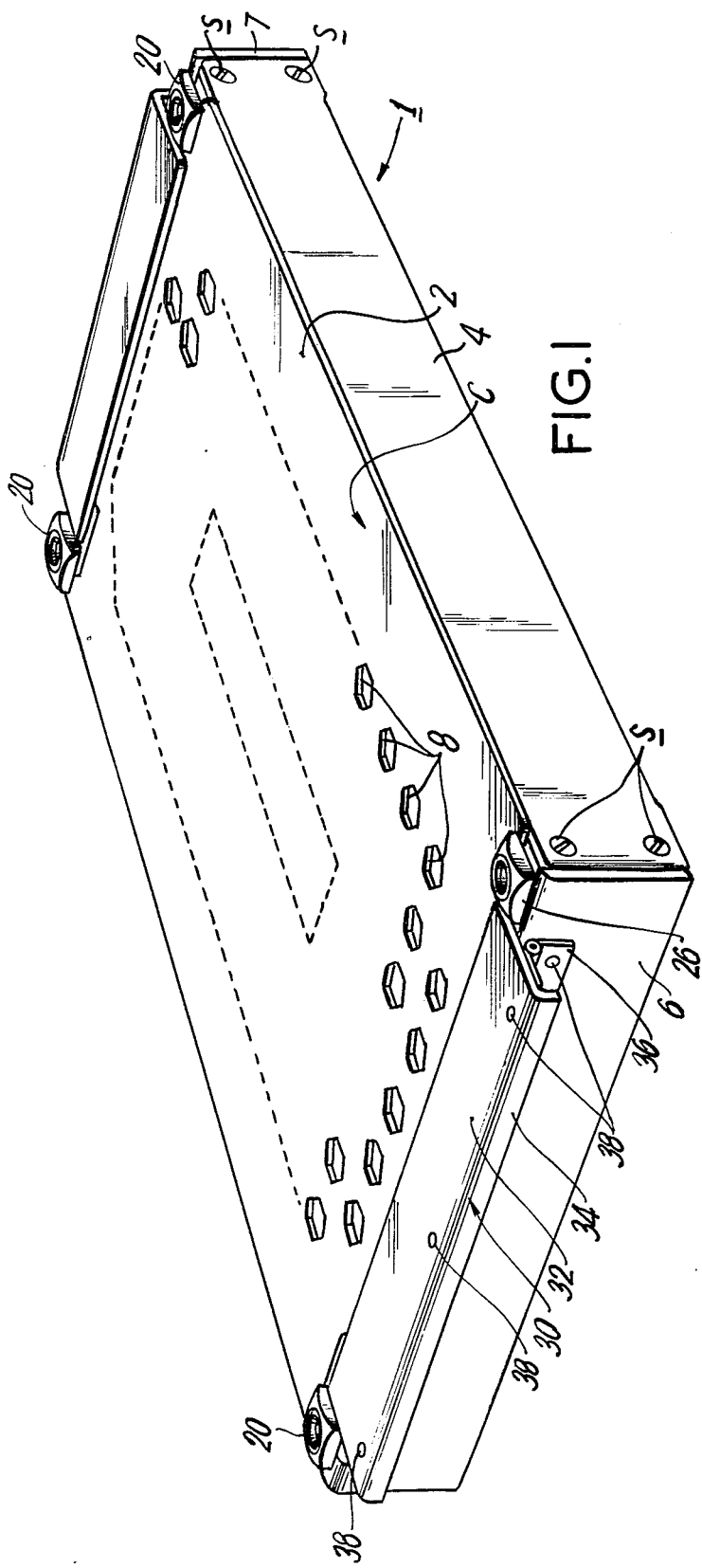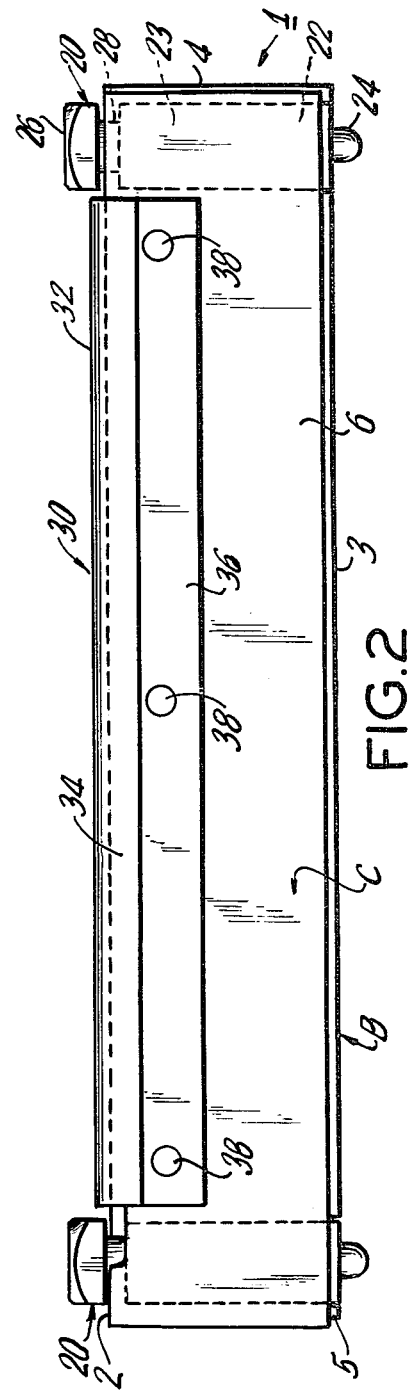

MEDICAL DEVICE STERILIZATION CASE

BACKGROUND OF THE INVENTION

The present invention relates to a structure for locking the cover of a medical device sterilization case.

SUMMARY OF THE INVENTION

It is an object of the present invention to provide a structure for the cover of a medical device sterilization case which will lock that cover in place automatically when the case is carried.

A medical device sterilization case made in accordance with the present invention comprises a top wall member being provided with a pair of attached, parallely opposed, depending side walls, a bottom wall member being provided with a pair of attached, parallely opposed, upstanding front and rear walls, at least four upstanding post members with a post member disposed at each side edge of the front and rear walls and attached to the front and rear walls and a handle member pivotally attached to each side wall with its axis of pivoting rotation and its longitudinal central axis disposed in parallel relation to the longitudinal central axis of its associated side wall and with a portion of it pivotally disposable between an adjacent post affixed to the front wall and an adjacent post affixed to the rear wall. Each post comprises a neck extending above the upper edge of the front and rear walls and a head surmounting said neck whose minimum transverse dimension is greater than the maximum transverse dimension of said neck. The top wall is provided with a pair of recesses extending rearwardly from its front edge (each recess being open to the front edge of said top wall and being provided with a concave extension at its rear edge configured to underly said head and restrain upward movement of said top wall) and a pair of apertures disposed adjacent its rear edge (each aperture being generally rectangular in top plan view and being provided with a concave extension at its rear edge configured to underly said head and restrain upward movement of said top wall). The longitudinal dimension of the handle is approximately equal to the distance between an adjacent post affixed to the front wall and an adjacent post affixed to the rear wall so that the handle, when disposed between any adjacent post affixed to the front wall and an adjacent post affixed to the rear wall, prevents rearward sliding movement of said top wall and its associated side walls.

BRIEF DESCRIPTION OF THE DRAWINGS

The preferred embodiment of the present invention will be described in detail with reference to the accompanying drawings in which:

FIG. 1 is a perspective view of a medical device sterilization case provided with the structure of the present invention, FIG. 2 is a side elevation view taken from the left hand side of FIG. 1 of the case of FIG. 1.

DESCRIPTION OF THE PREFERRED EMBODIMENTS

The medical device sterilization case of the present invention is provided with an improved handle structure for locking the case closed during carriage.

As illustrated in FIG. 1, the case 1 comprises a pair of rectangular, parallely opposed, top and bottom walls 2 and 3, respectively; a pair of rectangular, parallely opposed, front and rear walls 4 and 5, respectively; and a pair of rectangular, parallely opposed, side walls 6 and 7. Preferably, the top and bottom walls 2 and 3 are provided with a plurality of apertures to facilitate sterilization, only a few of which are shown in FIG. 1 for the sake clarity. In the form shown, the front, bottom and rear walls 4, 3 and 5 are formed of a single sheet of metal to form, a cover C, as are the top and side walls 2, 6 and 7 which form a base B.

Figure 5:
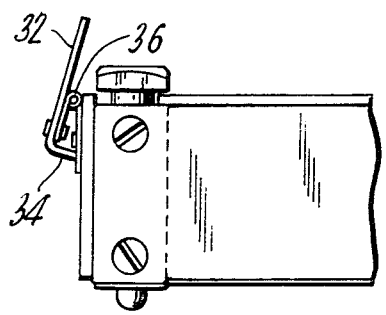
FIG. 5 is a fragmentary front elevation view of the case showing the handle in its unlocking position and FIG. 6 is a partially broken away, fragmentary, front elevation view of two cases stacked one on top of the other.
Figure 6:
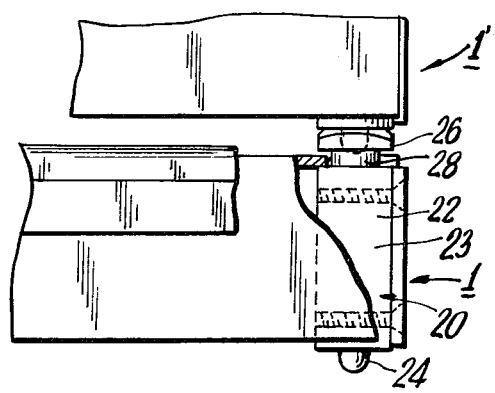

A post 20, (FIGS. 2 and 6) is attached to each side edge of the front and rear walls 4 and 5, such as by screws S to position the cover C (the bottom, front and rear walls 3, 4 and 5) with respect to the base B (the top and side walls 2, 6 and 7) and to aid in locking. Each post 20 comprises a body 22 having an upwardly extending, right rectangular prism configuration, a depending foot 24 and a head 26 connected to the top of the body 22 by a reduced diameter, cylindrical neck 28. The body 22 of each post 20 forms a corner support for the case 1, the side wall 23 (FIGS. 2 and 6) of the body 22 which confronts the depending side wall 6 or 7 acting, along with the side edge of the front and rear walls 4 and 5, to keep the cover C from slipping laterally. Each neck 28 is reduced in diameter and the minimum transverse dimension of the head 26 is greater than the maximum transverse dimension of the neck 28 so that the cutouts 10b and 12a can rest against the neck 28 and the head 26 will prevent upward movement of the top wall 2. The head 26 is square in top plan (FIGS. 3 and 4) but has its upper surface convexly curved in side elevation view (FIGS. 2, 5 and 6.) It is provided with a centrally disposed, hemispherically bottomed recess 27 (FIGS. 3 and 4)—so that a plurality of cases 1 and 1' (FIG. 6) can be stacked without them shifting horizontally. The foot 24 is itself configured to complement the configuration of the recess 27 in that it is generally cylindrical with a hemispherical tip. Each post 20 is secured to its respective front or rear wall 4 or 5 by a plurality of screws S.

Figure 3:
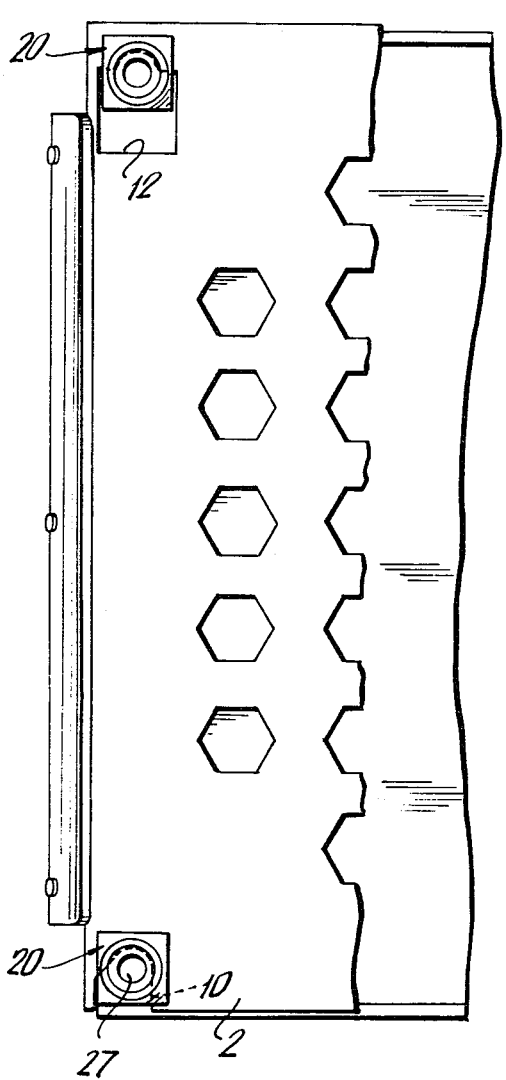
FIG. 3 is a fragmentary top plan view of the case showing the handle in its unlocking position.
Figure 4:
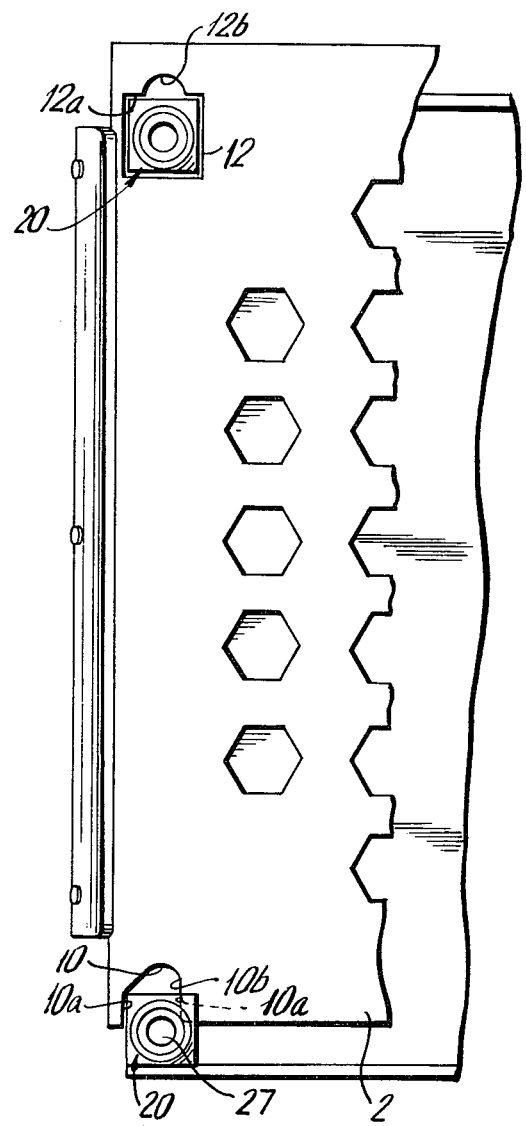
FIG. 4 is a fragmentary top plan view of the case showing the handle in its unlocking position and with the case cover shifted rearwardly.

As may be seen from FIGS. 3 and 4, the top wall 2 is provided with a pair of recesses 10 at its front edge and a pair of apertures 12 at its rear edge which coact with post 20 to permit the case to lock in a closed condition but still be openable. Each recess 10 is open at its front to the front edge of the top wall 2 and has parallel side edges 10a (FIG. 4) extending rearwardly from the front edge to a rear edge which has an offset concave, or preferably semicircular, cutout or extension 10b. Each aperture 12 is generally square in top plan except for its rear edge 12a (FIG. 4) which has a centered, concave, or preferably semicircular, cutout or extension 12b. Each aperture 12 is configured and dimensioned to permit the head 26 of a post 20 to pass axially through it. The depth of recess 10 is less than that of aperture 12, i.e., the distance from the rear edge of the cutout 10b to the front edge of the top wall 2 is less than that from rear edge of cutout 12b to the front edge of aperture 12, so that when the aperture 12 is clear to pass upwardly over the head 26 of its associated rear post 20 the recess 10 (and the front edge of the top wall 2) is not clear of the head 26 of its associated front post 20. The fact that the distance between side edges 10a of adjacent recesses is approximately equal to the distance between confronting points on the necks 28 of adjacent posts on the front wall 4 and the distance between side edges of adjacent apertures 12 is at least approximately equal to, if not greater than, the distance between confronting side edges of the heads 26 of adjacent posts 20 on the rear wall 5 also allows this pivoting.

A handle 30 (FIGS. 1 & 2) is pivotally attached by a hinge 36 to the upper edge of each side wall 6 and 7 with its axis of pivoting rotation and its longitudinal central axis disposed in parallel relation to the longitudinal central axis of the associated side wall to which it is secured, such as by fasteners 38. The handle 30 is generally L-shaped in end view (FIG. 5) with a depending lip 34 and a top plate 32 which has a length (FIG. 2) approximately equal to the distance between the confronting respective back and front edges of the heads 26 of the respective associated front and back posts 20.

With the cover C in its closed and locked condition (FIGS. 1 and 2) the case 1 has a right rectangular prism shape and the neck portions 28 of the two front posts 20 rest within the offset cutouts 10b of the two front recesses 10 and the neck portions 28 of the two rear posts 20 rest within the centered cutouts 12b of the two rear apertures 12 so that the head 26 of each post 20 prevents upward movement of the cover C (the top wall 2 and its associated side walls 6 and 7.) In this closed and locked condition, the top plate 32 of each handle 30 is disposed between a front and rear post 20 in generally parallel relation to the top wall 2 so that each top plate 32 and its associated front and rear posts 20 prevent rearward shifting of the cover C.

In order to open the case 1, the two handles 30 must be moved into their unlocking position by pivoting their lips 34 downwardly and top plates 32 upwardly. (See FIGS. 3 and 5.) This cannot be done easily when the case 1 is supported by its handles 30, thereby providing a safety feature to prevent undesired opening when the case 1 is being carried. When the handles 30 are so pivoted with the top plates 32 lifted clear of their interference with rearward shifting of the cover C, the cover C is slid rearwardly until the rear edge 12a of each rear aperture 12 clears the rear edge of the head 26 of each rear post 20. (See FIG. 4.) At this point the front edge of the top wall 2 has not cleared the rear edge of the head 26 of each front post 20. Next, the rear edge of the top wall 2 is pivoted upwardly using the top wall front edge-front post body upper surface contact as the pivot. During this operation the handles 30 may remain in their upward, unlocking position or they may be pivoted back to their downward locked position to provide a more secure grip on cover C in subsequent operations. As soon as the front edge of each rear aperture 12 clears the top surface of its associated rear post 20, the top wall 2 is slid rearwardly again until its front edge clears the rear edge of each front post 20. Alternatively, these two pivoting and sliding operations may be combined in one operation with both movements proceeding concurrently. At this point the rearward motion is continued (or alternatively, the cover C is lifted upwardly) to remove the cover C from the case 1.

In order to close and lock the case 1 the foregoing procedure is reversed.

While the present invention has been described in the context of its preferred embodiment, a medical device sterilization case, the term "medical device sterilization case" should be understood to include other cases for retaining articles during carriage.

While specific embodiments of the present invention have been shown and described in the specification and drawings to illustrate and explain the present invention, it should be understood that the present invention is not limited to these specific embodiments, but contemplates other embodiments falling within the scope of the following claims.

We claim:
1. A case comprising
   a top wall member being provided with a pair of attached, parallely opposed, depending side walls,
   a bottom wall member being provided with a pair of attached, parallely opposed, upstanding front and rear walls,
   at least four upstanding post members with a post member disposed at each side edge of the front and rear walls and attached to the front and rear walls, each post comprising a neck extending above the upper edge of the front and rear walls and a head surmounting said neck whose minimum transverse dimension is greater than the maximum transverse dimension of said neck, and
   a handle member pivotally attached to each side wall with its axis of pivoting rotation and its longitudinal central axis disposed in parallel relation to the longitudinal central axis of its associated side wall and with a portion of it pivotally disposable between an adjacent post affixed to the front wall and an adjacent post affixed to the rear wall,
   said top wall being provided with
   a pair of recesses extending rearwardly from the front edge of said top wall, each recess being open to the front edge of said top wall and being provided with a concave extension at its rear edge configured to underly said head and restrain upward movement of said top wall and
   a pair of apertures disposed adjacent the rear edge of said top wall, each aperture being generally rectangular in top plan view and being provided with a concave extension at its rear edge configured to underly said head and restrain upward movement of said top wall,
   the longitudinal dimension of said handle being approximately equal to the distance between an adjacent post affixed to the front wall and an adjacent post affixed to the rear wall so that said handle, when disposed between an adjacent post affixed to the front wall and an adjacent post affixed to the rear wall, prevents rearward sliding movement of said top wall and its associated side walls.
2. A case in accordance with claim 1, wherein
   the distance from the rear edge of the extension of said recess to the front edge of said top wall is less than the distance from the rear edge of the extension of said aperture to the front edge of said aperture and
   the distance between side edges of adjacent recesses is approximately equal to the distance between confronting points on the necks of adjacent posts on the front wall and the distance between side edges of adjacent apertures is at least approximately equal to the distance between confronting side edges of the heads of adjacent posts on the rear wall so that, when the posts on said rear wall are aligned with their associated apertures and in position for the top wall to move upwardly, a portion of the front edge of said top wall may make pivotal contact with the post on said front wall.

3. A case in accordance with claim 1, wherein each post is provided with a centrally disposed foot depending from its body and each head is provided with a centrally disposed recess, said recess and the lower extremity of said foot being complementarily configured to permit the foot of a post to fit into the recess of an identically configured post.

* * * * *